(12) United States Patent
Brock et al.

(10) Patent No.: US 7,223,100 B2
(45) Date of Patent: *May 29, 2007

(54) ENDODONTIC INSTRUMENT HAVING NOTCHED CUTTING SURFACES

(76) Inventors: G. Matthew Brock, 1403 Patten Rd., Lookout Mountain, GA (US) 30750; John T. McSpadden, 1403 Patten Rd., Lookout Mountain, GA (US) 30750

( * ) Notice: Subject to any disclaimer, the term of this patent is extended or adjusted under 35 U.S.C. 154(b) by 0 days.

This patent is subject to a terminal disclaimer.

(21) Appl. No.: 11/130,824

(22) Filed: May 17, 2005

(65) Prior Publication Data

US 2005/0266375 A1 Dec. 1, 2005

Related U.S. Application Data

(63) Continuation of application No. 10/219,927, filed on Aug. 15, 2002, now Pat. No. 6,966,774.

(60) Provisional application No. 60/312,823, filed on Aug. 16, 2001.

(51) Int. Cl.
*A61C 5/02* (2006.01)
(52) U.S. Cl. ..................................... 433/102
(58) Field of Classification Search ............... 433/102, 433/165
See application file for complete search history.

(56) References Cited

U.S. PATENT DOCUMENTS

| | | |
|---|---|---|
| 251,598 A | 12/1881 | Johanson |
| 1,402,229 A | 1/1922 | Hauptmeyer |
| 5,035,617 A | 7/1991 | McSpadden |
| 5,104,316 A | 4/1992 | McSpadden |
| 5,106,298 A | 4/1992 | Heath et al. |
| 5,236,357 A | 8/1993 | Randin |
| 5,380,200 A | 1/1995 | Heath et al. |
| 5,429,504 A | 7/1995 | Peltier et al. |
| 5,464,362 A | 11/1995 | Heath et al. |
| 5,569,035 A | 10/1996 | Balfour et al. |
| 5,746,597 A | 5/1998 | Maillefer et al. |
| 5,842,862 A | 12/1998 | Nissan |
| 6,149,501 A | 11/2000 | Farzin-Nia et al. |
| 6,238,491 B1 | 5/2001 | Davidson et al. |
| 6,267,592 B1 | 7/2001 | Mays |
| 6,315,558 B1 | 11/2001 | Farzin-Nia et al. |
| 6,390,813 B1 | 5/2002 | Farzin-Nia et al. |
| 6,419,488 B1 | 7/2002 | McSpadden et al. |
| 6,428,317 B1 | 8/2002 | Abel |
| 6,431,863 B1 | 8/2002 | Sachdeva et al. |
| 6,443,730 B2 | 9/2002 | Davidson |
| 6,514,076 B1 | 2/2003 | Bleiweiss et al. |

FOREIGN PATENT DOCUMENTS

EP  0 120 542  10/1984

*Primary Examiner*—Cary E. O'Connor
(74) *Attorney, Agent, or Firm*—Luedeka, Neely & Graham, P.C.

(57) ABSTRACT

A fluteless endodontic file is provided, formed from a tapered shaft of material having a prismatic shape generally defined by three or more side surfaces and three or more interposed corners. A plurality of notches are cut into one or more corners defining cutting surfaces, points and/or edges. The notched cutting surfaces are formed such that the file, when rotated and/or reciprocated within a root canal, effectively cuts/debrides hard tissue (known in the art as dentin) as well as soft tissue, thus, forming an optimal canal shape. The cutting surfaces are also preferably formed at an angle to the centerline of the instrument to provide optimal cutting efficiency and material removal. The fluteless file design exhibits increased efficacy, with less tendency to bind and break within the root canal and also significantly reduces manufacturing and capital equipment costs.

19 Claims, 7 Drawing Sheets

ENDODONTIC INSTRUMENT HAVING NOTCHED CUTTING SURFACES

RELATED APPLICATIONS

This application is a continuation of U.S. patent application Ser. No. 10/219.927, filed Aug. 15. 2002, now U.S. Pat. No. 6,966,774, which claims priority under 35 U.S.C. § 120(e) to provisional application Ser. No. 60/312,823 filed Aug. 16, 2001, which is incorporated herein by reference.

BACKGROUND OF THE INVENTION

1. Field of the Invention

The present invention relates generally to the field of dentistry and more particularly to a fluteless endodontic instrument having notched cutting surfaces for cleaning and enlarging a root canal.

2. Description of the Related Art

In the field of endodontics, one of the most important and delicate procedures is that of cleaning or extirpating a root canal to provide a properly dimensioned cavity while essentially maintaining the central axis of the canal. This step is important in order to enable complete filling of the canal without any voids and in a manner which prevents the entrapment of noxious tissue in the canal as the canal is being filled.

In a root canal procedure, the dentist removes injured tissue and debris from the canal prior to filling the canal with an inert filling material. In performing this procedure the dentist must gain access to the entire canal, shaping it as necessary. But root canals normally are very small in diameter, and they are usually quite curved. It is therefore very difficult to gain access to the full length of a root canal.

Many tools have been designed to perform the difficult task of cleaning and shaping root canals. Historically, dentists have used a wide multitude of tools to remove the soft and hard tissues of the root canal. These tools, usually called endodontic files, have been made by three basic processes. In one process, a file is have been made by three basic processes. In one process, a file is created by twisting a prismatic rod of either square or triangular cross section in order to create a file with helical cutting/abrading edges ("K-file"). The second process involves grinding helical flutes into a circular or tapered rod to create a file with one or more helical cutting edges ("Hedstrom file"). The third method involves "hacking" or rapidly striking a circular or tapered rod with a blade at a given angle along the length of the rod, thus creating an endodontic file characterized by a plurality of burr-like barbs or cutting edge projections ("barbed file" or "broach"). Each of these methods produces an instrument having unique attributes, advantages, and disadvantages.

Endodontic files have historically been made from stainless steel, but due to the inherent stiffness and brittleness of steel, these tools can sometimes pose a significant danger of breakage in the curved root canal. More recent designs have attempted to overcome these problems. Some attempt to alter the geometry of the stainless steel file in order to provide more flexibility. This approach has had only limited success, and the stainless steel tools still have a tendency to break if over-torqued or fatigued.

A series of comparative tests of endodontic instruments made of nickel-titanium alloy (Nitinol™ or NiTi) and stainless steel were conducted and published in an article entitled "An Initial Investigation of the Bending and the Torsional Properties of Nitinol Root Canal Files," Journal of Endodontics, Volume 14, No. 7, Jul. 1988, pages 346-351. The Nitinol instruments involved in these tests were manufactured in accordance with fabrication procedures and operating parameters conventionally used in the machining of stainless steel endodontic instruments. This process involved grinding a helical flute in a tapered shaft to form helical cutting edges.

The reported tests demonstrated that the NiTi instruments produced by the described machining process exhibited superior flexibility and torsional properties as compared to stainless steel instruments, but the cutting edges of the instruments exhibited heavily deformed metal deposits which, according to the article, rendered the instruments generally unsatisfactory for clinical use.

In general, alloys of nickel (Ni) and titanium (Ti) have a relatively low modulus of elasticity (0.83 GPa) over a wide range, a relatively high yield strength (0.195-690 MPa), and the unique and the unusual property of being "superelastic" over a limited temperature range. Superelasticity refers to the highly exaggerated elasticity, or spring-back, observed in many NiTi and other superelastic alloys over a limited temperature range. Such alloys can deliver over 15 times the elastic motion of a spring steel, i.e., withstand twisting or bending up to 15 times greater without permanent deformation The particular physical and other properties of Nitinol alloys may be varied over a wide range by adjusting the precise Ni/Ti ratio used. However, the superelastic properties of NiTi also make the material very difficult and expensive to machine.

Machining of NiTi tools for endodontic use has been an area of significant development efforts in recent years. For example, U.S. Pat. No. 5,464,362 to Heath et. al. describes a method of grinding a rod of a nickel-titanium alloy in order to create a fluted file. However, current state-of-the art manufacturing processes remain relatively expensive and slow and require sophisticated 6-axis grinding machines and the like.

Accordingly, there is a need for an improved endodontic file design which will allow for more economical manufacture of an endodontic tool from nickel titanium and other suitable alloys.

SUMMARY OF THE INVENTION

It is therefore an object of the present invention to provide an improved endodontic file design and method of manufacturing such files from nickel-titanium alloys, stainless steel and/or other materials. It is another object of the invention to provide an endodontic instrument having a reduced tendency to break during use. It is another object of the invention to improve the efficacy of an endodontic instrument and/or to reduce the number of instruments necessary to enlarge a root canal. Still another object of the invention is to provide an endodontic instrument which can be quickly and economically manufactured using conventional 3-axis grinding machines.

According to one embodiment of the present invention, a fluteless endodontic file is provided, formed from a generally prismatic rod (e.g., having multiple flats and interposed sharp corners) preferably tapered along its length. A plurality of notches are cut into the exposed corners in an alternating regular and/or irregular pattern defining cutting surfaces, points and/or edges. The notched cutting surfaces are formed such that the file, when rotated and/or reciprocated within a root canal, effectively cuts/debrides hard tissue (known in the art as dentin) as well as soft tissue, thus, forming an optimal canal shape. The cutting surfaces are also preferably formed at an angle to the centerline of the instrument to provide optimal cutting efficiency and material removal. A dental instrument having features and advantages of the present invention may be generally characterized as having a prismatic shape with multiple vertically aligned notched cutting surfaces preferably formed at an angle from the centerline of the shaft. The design exhibits increased flexibility and efficacy, has less tendency to bind and break within the root canal and significantly reduces manufacturing and capital equipment costs.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention and its essential features and advantages, certain preferred embodiments and modifications thereof will become apparent to those skilled in the art from the detailed description herein having reference to the figures that follow, of which.

DETAILED DESCRIPTION OF THE PREFERRED EMBODIMENTS

Figure 1:
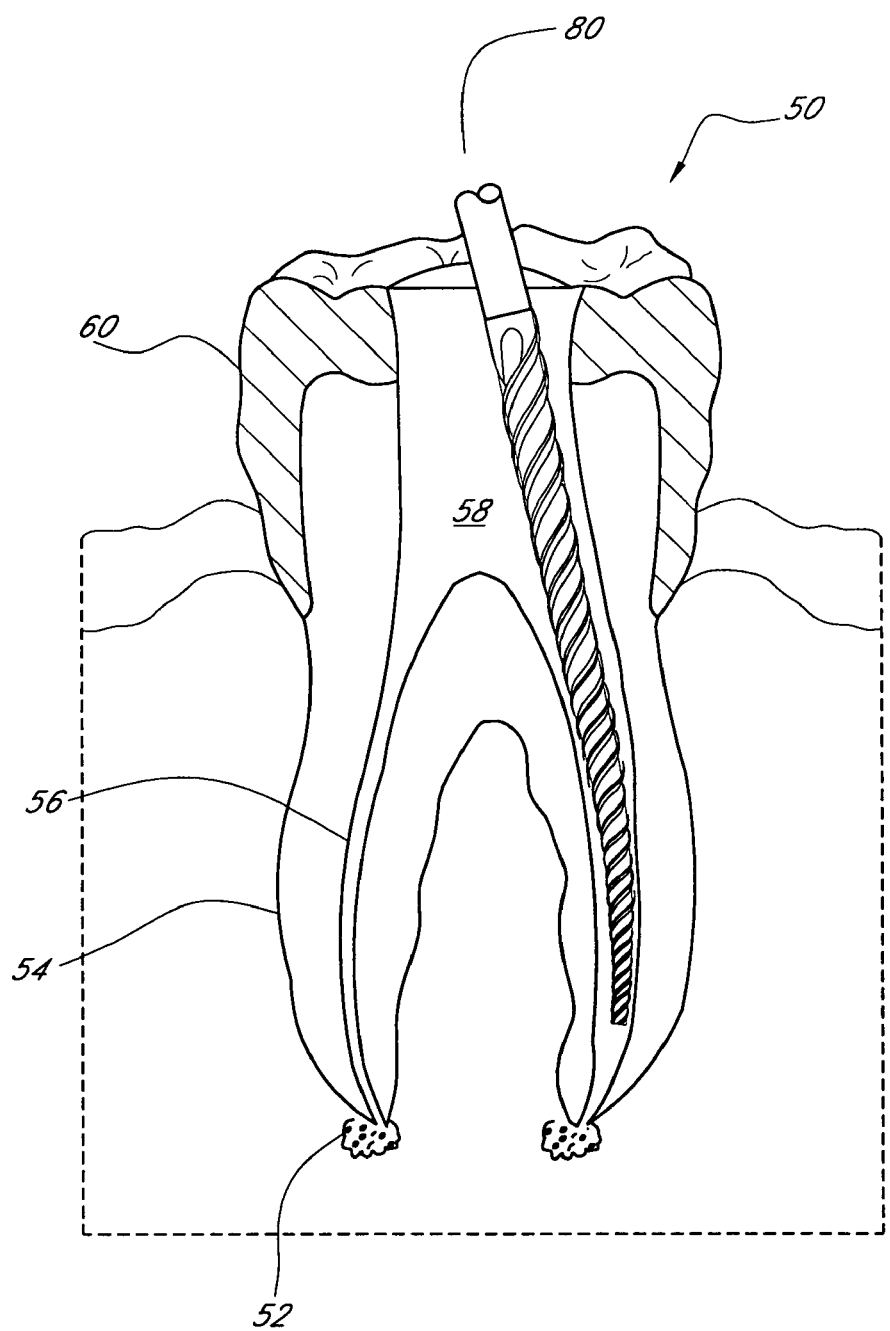
FIG. 1 is a section view of a tooth and root structure illustrating the use of a conventional fluted endodontic instrument for performing a typical root canal procedure.

FIG. 1 is a partial cross section of a tooth 50 and supporting root structure illustrating the use of a typical fluted endodontic file 80 to carry out a standard root canal procedure. The root canal 56 of a tooth houses the circulatory and neural systems of the tooth. These enter the tooth at the terminus 52 of each of its roots 54 and extend through a narrow, tapered canal system to a pulp chamber 58 adjacent the crown portion 60 of the tooth. If this pulp tissue becomes diseased or injured, it can cause severe pain and trauma to the tooth, sometimes necessitating extraction of the tooth. Root canal therapy involves removing the diseased tissue from the canal 56 and sealing the canal system in its entirety. If successful, root canal therapy can effectively alleviate the pain and trauma associated with the tooth so that it need not be extracted.

To perform a root canal procedure, the endodontist first drills into the tooth 50 to locate the root canal(s) 56 and then uses an endodontic file or reamer instrument 80 to remove the decayed, injured or dead tissue from the canal. These instruments are typically elongated cutting or abrading instruments which are rotated and/or reciprocated within the root canal either by hand or using a slow speed drift. The primary goal is to remove all of the decayed or injured pulp tissue while leaving the integrity of the central axis of the root canal relatively unaffected. Proper cleaning and shaping of the root canal 56 is important in order to allow complete filling of the root canal void in a homogenous three dimensional manner such that leakage or communication between the root canal system and the surrounding and supporting tissues of the tooth 50 is prevented. Once as much of the diseased material as practicable is removed from the root canal, the canal 56 is sealed closed, typically by reciprocating and/or rotating a condenser instrument in the canal to urge a sealing material such as gutta-percha into the canal.

One of the primary challenges in performing root canal therapy is that the root canals are not necessarily straight and are often curved or convoluted. Therefore, it is often difficult to clean the canal while preserving its natural shape. Many instruments (particularly the older, stainless steel instruments) have a tendency to straighten out the canal or to proceed straight into the root canal wall, altering the natural shape of the canal. In some extreme cases, the instrument may transport completely through the canal wall causing additional trauma to the tooth and/or surrounding tissues. Also, the openings of many root canals are small, particularly in older patients, due to calcified deposits on the root canal inner walls. Thus the files or reamers must be able to withstand the torsional load necessary to penetrate and enlarge the canal opening without breaking the instrument, as may also occasionally occur with the older stainless steel endodontic files.

To alleviate the transportation and breakage problems, highly flexible endodontic files fabricated from nickel-titanium alloy (Nitinol™ or NiTi) were introduced and have become widely accepted. See, e.g. U.S. Pat. No. 5,882,198, incorporated herein by reference. But conventional fluted instrument designs are difficult to manufacture from Nitinol alloys, often requiring expensive grinding operations and specialized 6-axis grinding machines to create the desired continuous helical fluting and sharp cutting edges. Conventional fluted instruments 80 also suffer from an occasional tendency to bind and/or to advance unpredictably into the root canal 56 by virtue of a "screwing-in" effect as the instrument is rotated. In many cases, this binding or screwing-in effect can result in the file breaking inside the canal. In the most severe cases, the fluted instrument 80 can actually drive itself through the terminus of the canal 56 and into the patient's jaw bone and surrounding soft tissues.

FIGS. 2A-G illustrate one preferred embodiment of a fluteless endodontic file having features and advantages of the present invention. The file 100 generally comprises a shaft 110 having a shank portion 104 and an elongated working portion 106. The working portion 106 extends from a proximal end 107 adjacent the base of the shank 104 to a distal end 108 terminating in a tip 150. The shank portion 104 preferably includes a fitting portion 109 for mating with the chuck of a dental handpiece (not shown). The fitting portion 109 includes a generally I-shaped flat side 182 which defines a step 184 and a generally semicircular disk 186 above and adjacent to a generally semi-circular groove 188. Such fitting 109 is typical of those employed in the dental industry for connecting or interfacing a dental tool with dental drill or handpiece.

Alternatively and/or in addition to the fitting portion 109, the shank portion 104 may include a knurled or otherwise treated surface (not shown) or handle to facilitate hand manipulation of the file 100. Thus, the instrument 100 may either be used by manipulating the instrument manually in a rotating or reciprocating action, or the instrument may be manipulated by attaching the fitting portion 109 of the instrument to a motorized handpiece for effecting more rapid removal of tissue from the root canal, as desired.

The working portion 106 of the instrument 100 preferably has a length ranging from about 3 mm to about 18 mm. A standard length is about 16 mm. The working portion 106 may have a constant cross-sectional diameter or, more preferably, it is tapered from the proximal end 107 to the distal end 108, as shown. In the particular embodiment shown, the taper is substantially uniform—that is, the rate of taper is constant along the working portion 106. A preferred taper rate ranges from about 0.01 mm/mm to about 0.12 mm/mm and may be constant or varied along the length of the working portion 106.

The shank 110 is preferably formed from a rod of nickel titanium alloy, such as SE508 nickel-titanium wire manufactured by Nitinol Devices and Components, Inc. of Fremont, Calif. This is a typical binary nickel-titanium alloy used for endodontic files and comprises about 56% nickel and about 44% titanium by weight. Table 1, below, summarizes certain selected material properties of the SE508 NiTi alloy:

TABLE 1

| SE508 MATERIAL PROPERTIES | |
| --- | --- |
| PHYSICAL PROPERTIES | |
| Melting Point | 1310° C. |
| Density | 6.5 g/cm3 |
| Electrical Resistivity | 82 µohm-cm |
| Modulus of Elasticity | 75 x 10^6 MPa |
| Coefficient of Thermal Expansion | 11 x 10-6/° C. |
| MECHANICAL PROPERTIES | |
| Ultimate Tensile Strength (UTS) | 1150 Mpa |
| Total Elongation | 10% |
| SUPERELASTIC PROPERTIES | |
| Loading Plateau Stress @ 3% strain | 450 MPa |
| Superelastic Strain (max) | 8% |

TABLE 1-continued

| SE508 MATERIAL PROPERTIES | |
| --- | --- |
| Permanent Set (after 6% strain) | 0.2% |
| Transformation Temperature (Af) | 5–18° C. |
| COMPOSITION | |
| Nickel (nominal) | 55.8 wt. % |
| Titanium (nominal) | 44.2 wt. % |
| Oxygen (max) | 0.05 wt. % (max) |
| Carbon (max) | 0.02 wt. % (max) |

If desired, special heat treatments may be employed and/or trace elements of oxygen (O), nitrogen (N), iron (Fe), aluminum (Al), chromium (Cr), cobalt (Co) vanadium (V), zirconium (Zr) and/or copper (Cu), may be added to achieve desired mechanical properties. See, for example, U.S. Pat. No. 5,843,244 to Pelton, incorporated herein by reference. While nickel-titanium alloys are preferred, the invention disclosed herein is not limited as such, but may be practiced using a wide variety of other suitable alloys, including other super-elastic alloys and conventional medical-grade steel or nickel alloys.

Figure 2A:
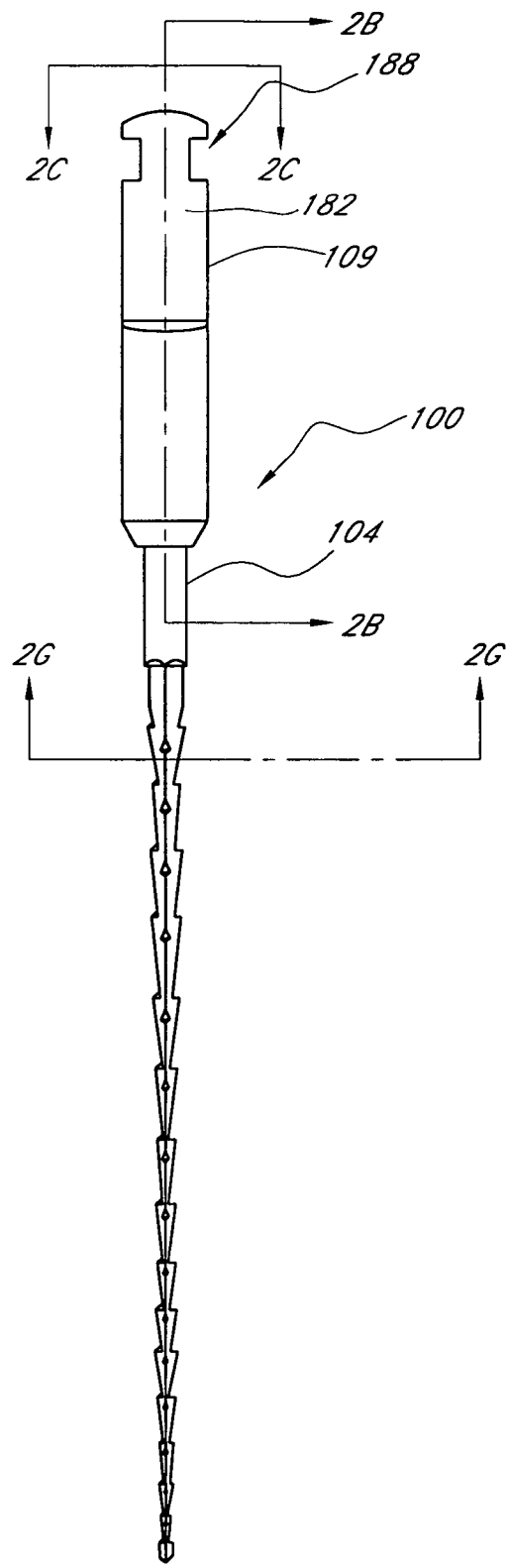
FIG. 2A is a side elevation view of a fluteless endodontic instrument having features and advantages of the present invention.
Figure 2B:
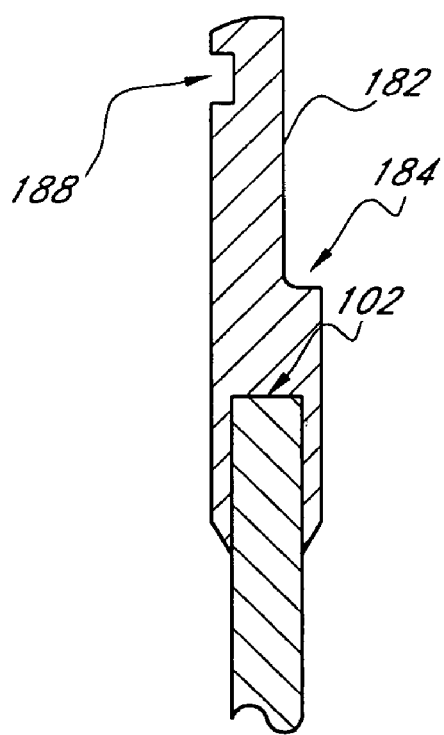
FIG. 2B is a partial cross-section detail view of the fitting portion of the fluteless endodontic instrument of FIG. 2A.
Figure 2C:
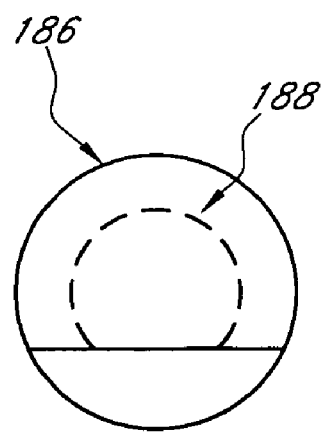
FIG. 2C is a top plan view of the fitting portion of the fluteless endodontic instrument of FIG. 2A.
Figure 2D:
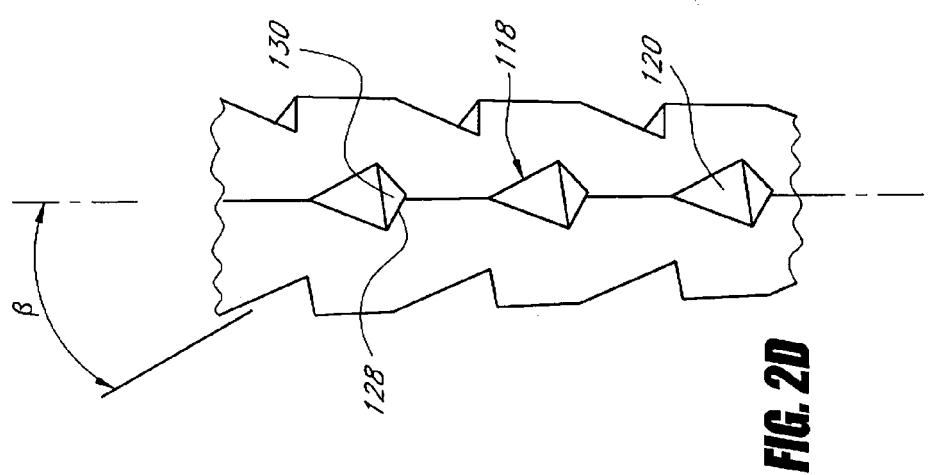
FIG. 2D is a detail view of the working portion of the fluteless endodontic instrument of FIG. 2A, illustrating multiple vertically aligned notched cutting surfaces formed thereon.
Figure 2E:
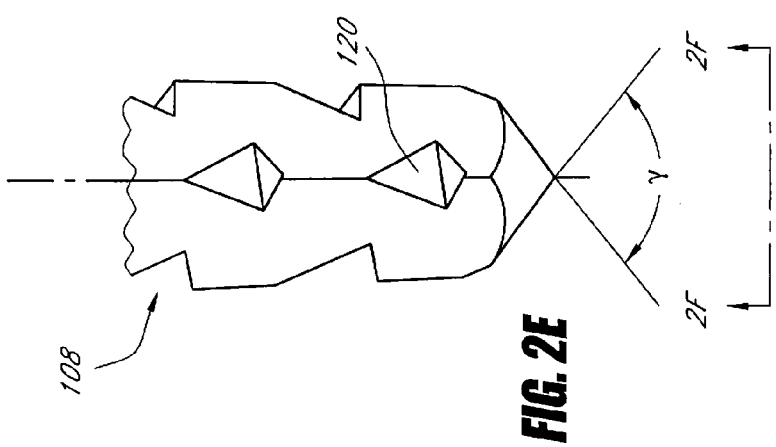
FIG. 2E is a detail view of the distal portion of the fluteless endodontic instrument of FIG. 2A, illustrating the tip geometry thereof.
Figure 2F:
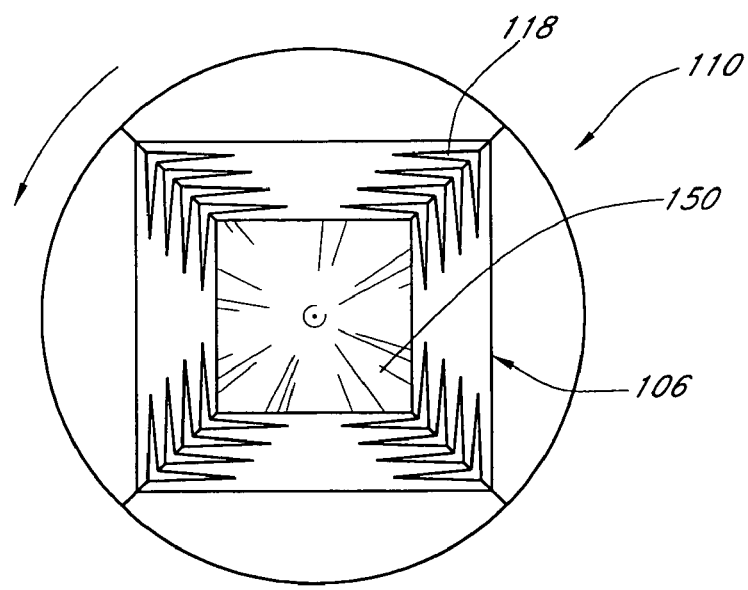
FIG. 2F is a bottom plan view of the working portion of the fluteless endodontic instrument of FIG. 2A.
Figure 2G:
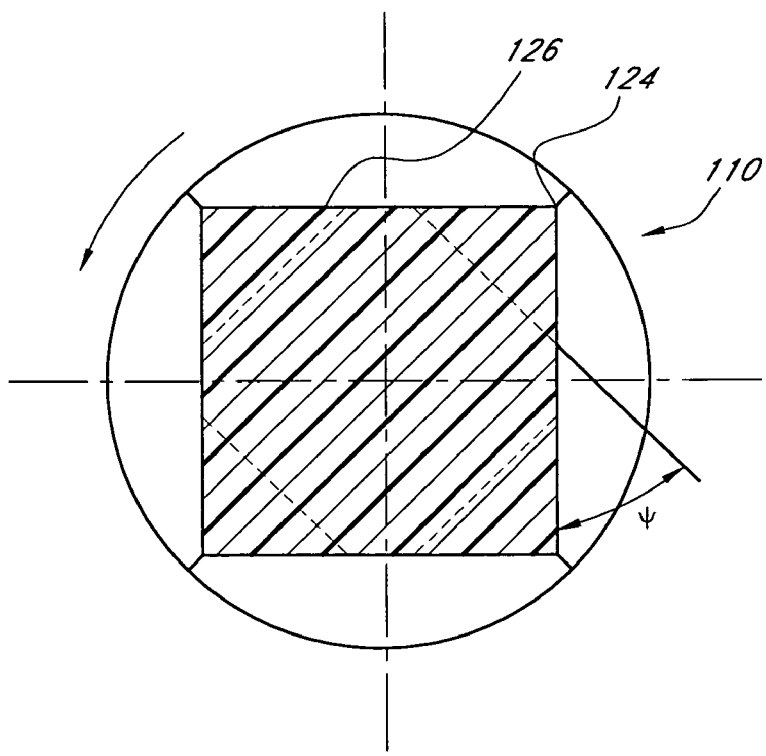
FIG. 2G is a partial cross-section view of the working portion of the fluteless endodontic instrument of FIG. 2A.

The shaft 110 is preferably rolled, ground, extruded or otherwise machined to produce an elongated prismatic structure having a substantially constant or tapering geometric shape in cross-section. A square cross-section is particularly preferred, having four flat facing surfaces ("flats") 126 and four corners 124 (preferably sharp), as illustrated in FIG. 2G. Of course, those skilled in the art will readily appreciate that a wide variety of other shapes may also be used with efficacy, such as triangular, hexagonal, octagonal rectangular, or other regular polygon. Certain irregular polygons may also be used with efficacy such as those formed with one or more exposed corners and one or more facing surfaces (flat or otherwise). Also, the shape can vary and/or alternate along the length of the instrument, as desired.

A plurality of notches 118 are formed along each corner 124 of the shaft 110 defining cutting planes 130, cutting edges 128 and relief surfaces 120. Notches 118 are preferably vertically aligned and formed in a regular spaced pattern 124 along each corner 124. Preferably, notches 118 are registered relative to notches formed on adjacent corners such that as the instrument 100 is rotated clockwise each successive corner 124 presents a notch 118 and a cutting plane 128 that is successively higher and higher up the working portion 106 of the shank 104 from distal end 108 to the proximal end 107. Advantageously, in this manner the cutting edges 128 cut or abrade against the root canal wall, expanding the canal opening while successively urging removed and dislodged tissues upward out of the canal. Of course, those skilled in the art will readily appreciate that various alternative notch patterns may be employed, including forming notches 118 on alternating and/or selected corners 124 only, forming notches 118 in a regular or irregular spaced pattern on one or more selected corners 124, alternating the size, spacing, angle and placement of notches 118 on selected corners 124 to achieve any number of desired effects. Notches 118 may be substantially uniform in depth or, more preferably, notches 118 increase in depth from the distal end 108 to the proximal end 107 to provide optimal cutting and tissue removal as well as instrument flexibility.

If desired, notches 118 may be angled or otherwise formed to provide cutting edges 128 with a desired rake angle. Thus, preferably the cutting planes 130 are formed at an angle α with respect to the longitudinal axis of between about 60° and 120°, more preferably between about 95° and 115° and most preferably about 105°. In an alternative embodiment, the cutting planes 130 may be formed at an angle α with respect to the longitudinal axis of between about 90° and 170°, more preferably between about 110° and 160° and most preferably about 120°. The relief surface 120 is preferably formed at an angle β with respect to the longitudinal axis of between about 5° and 45°, more preferably between about 10° and 20° and most preferably about 15°. The relief surface 120 may also be formed at any desired angle ψ with respect to an adjacent flat surface 126. An angle ψ of about 45° is chosen in the preferred embodiment illustrated in FIG. 2G. Of course, those skilled in the art will appreciate how the particular notch geometries can be varied to produce desired effects without departing from the essential teachings disclosed herein.

The tip 150 of the instrument 100 may assume any number of a variety of possible configurations (e.g., chisel, cone, bullet, multi-faceted and/or the like), depending upon the preference of the endodontist and manufacturing conveniences. In the illustrated embodiment, the tip 150 is formed as a simple cone, as illustrated in FIGS. 2E and 2F. The conical tip 150 preferably has an included cone angle γ of between about 45° and 120°, more preferably between about 60° and 100° and most preferably about 75°. The surface of the tip 150 may be uninterrupted and/or one or more notches 118 may extend into the tip 150 to form one or more additional cutting edges, as desired. Again, those skilled in the art will readily appreciate how the particular geometries can be varied without departing from the essential teachings disclosed herein.

Advantageously, the fluteless file 100 according to the preferred embodiment described above is highly efficacious in cleaning and expanding root canal openings. The notches 118 and cutting surfaces 130 formed thereby are more effective in scraping away and removing hard and soft tissues from the root canal. The notched design also reduces friction and improves the flexibility of the file for a given material and cross-section, allowing larger diameter files to be used in highly curved root canals. This improves the speed and efficacy of the root canal procedure and reduces the number of endodontic files and other specialized tools required to complete each procedure. The disclosed file design is also significantly less expensive to manufacture than conventional fluted files due to its relatively simple design and, most notably, the lack of helical flutes. The fluteless endodontic file design according to the above-described embodiment can be easily and expeditiously fabricated from stainless steel or nickel-titanium alloys using a standard 3-axis grinding machine with or without a rotating chuck. Because comparatively little material need be removed in grinding the file 100 from a tapered square or other prismatically-shaped blank, the overall grinding operation is significantly streamlined and requires less redressing and replacing of worn grinding wheels. The lack of helical flutes also diminishes the possibility of canal transportation and eliminates the possibility of the file 100 advancing unpredictably into the root canal by virtue of a "screwing in" effect. If the tip 108 were to bind or lodge in the canal, the working portion 106 of the file 100 would twist, effectively forming a reverse helix and thereby urging the file out of the canal. Thus, the overall safety of the root canal procedure is improved.

Figure 3A:
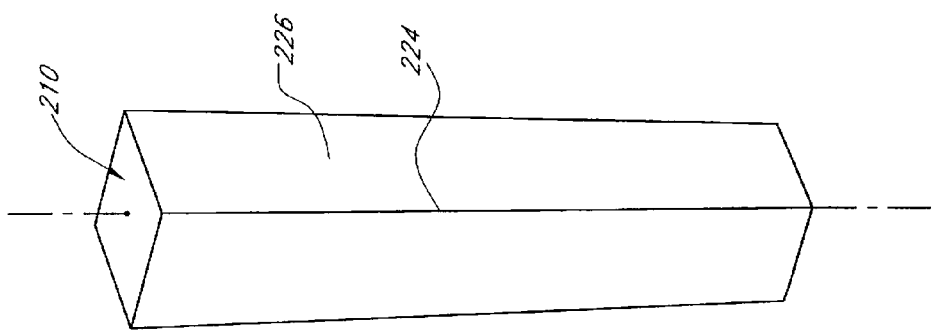
FIG. 3A-C are time-sequenced isometric views illustrating one preferred method for manufacturing a fluteless endodontic instrument having features and advantages of the present invention.
Figure 3B:
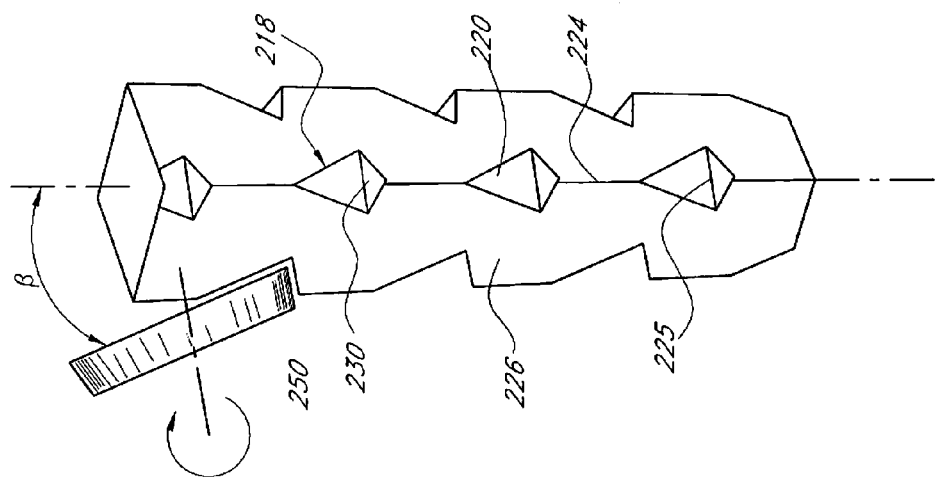
Figure 3C:
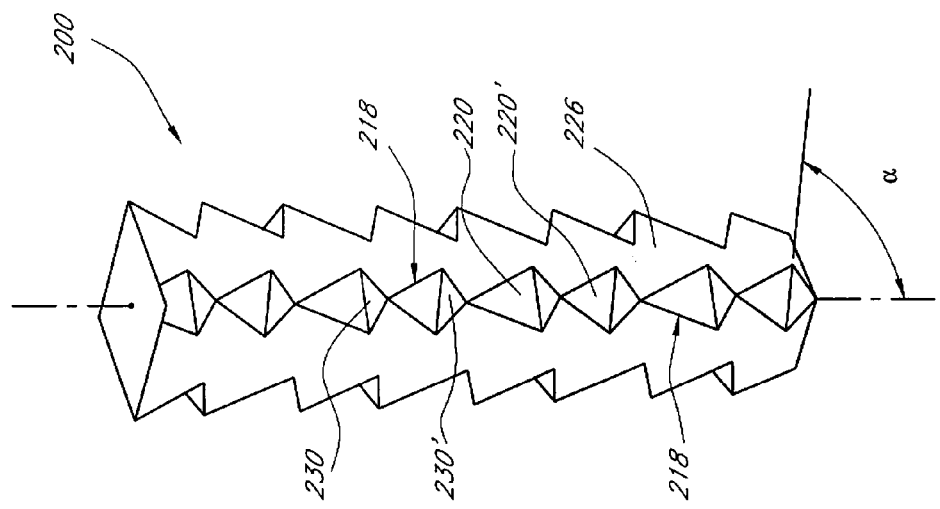

FIGS. 3A-C are time-sequenced schematic views illustrating one preferred method of manufacturing a fluteless endodontic instrument having features and advantages of the present invention. FIG. 3A shows a tapered blank shaft 210 having a desired, generally prismatic shape—in this case a square having four flats 226 and an equal number of interposed corners 224. The shaft preferably comprises a stainless steel or Nickel-Titanium alloy. The shaft 210 can be shaped from a length of wire by rolling, extruding, grinding or other machining operations to reduce its cross-section and produce the desired tapered, generally prismatic shape. If sharp edges are desired at corners 224, then a final grinding operation is preferably performed to achieve a smooth ground surface on each flat 226. Of course, those skilled in the art will readily appreciate that "flats" 226 may not necessarily be flat, but may have a rounded, curved, convex and/or concave features, as may be desired. However flat surfaces are particular preferred for manufacturing expedience.

Once the blank 210 is suitably shaped, successive grinding operations are preferably carried out using a rotating grinding wheel 250 to form a plurality of substantially vertically-aligned notches 218 on one or more corners 224, as illustrated in FIG. 3B. These notches may be formed using either high-speed or slow-speed grinding operations carried out using a conventional 3-axis grinding machine in accordance with well-documented grinding techniques. Any number of such notches 118 may be formed in this manner, as desired.

The wheel 250 may be dressed, shaped and/or manipulated relative to the work piece in any suitable manner desired to produce corresponding ground cutting surfaces 220 and 230, as illustrated. A flat grinding wheel 250 manipulated along a linear cutting path is particularly preferred for manufacturing expedience. Preferably, the wheel 250 is inclined at an angle β with respect to the longitudinal axis of the shaft 210 to produce a desired inclination of recessed surfaces 220. Of course, those skilled in the art will readily appreciate that other specialized shapes and/or more sophisticated wheel manipulation techniques may be used to create rounded, radiused, and/or filleted surfaces 230, 220, as desired. For example, the wheel 250 may be suitably dressed or radiused along one corner to produce a rounded surface and/or filleted corner instead of the sharp recessed corners 225 illustrated in FIG. 3B. The perimeter surface of the wheel 250 may be dressed square with the facing surface or it may be angled, as desired.

Preferably, the grinding wheel 250 is moved past the work piece 210 (or vice-versa) in such a manner that notches 218 are formed with a sloped cutting surface 230 producing an angle $α_1$ of between about 50° and 110°, more preferably between about 70° and 90°, and most preferably about 80° with respect to the longitudinal axis of the shaft 210, as indicated in FIGS. 3B, 3C. IN an alternative preferred embodiment, the grinding wheel 250 is moved past the work piece 210 (or vice-versa) in such a manner that notches 218 are formed with a sloped cutting surface 230 producing an angle $α_1$ of between about 20° and 110°, more preferably between about 25° and 80°, and most preferably about 60° with respect to the longitudinal axis of the shaft 210 If desired, additional notches 218' may be formed with sloped cutting surfaces 230' having an angle $α_2$ of between about 70° and 130°, more preferably between about 90° and 110°, and most preferably about 100° with respect to the longitudinal axis of the shaft 210, as indicated in FIG. 3C. In this manner, the fluteless instrument 200 is equally effective when rotated in either a clockwise or counterclockwise direction, with or without reciprocation. Of course, those skilled in the art will readily appreciate that the particular number, placement and geometries of the notches 218, 218' and the resulting exposed cutting surfaces 220, 220', 230, 230' may be varied without departing from the scope and spirit of the invention disclosed herein.

Figure 4A:
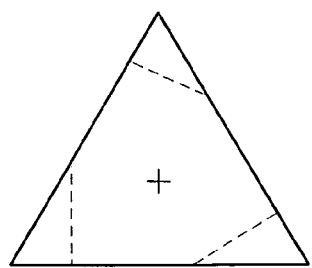
FIGS. 4A-H are schematic views of various alternative embodiments of fluteless endodontic instruments having features and advantages of the present invention.
Figure 4B:
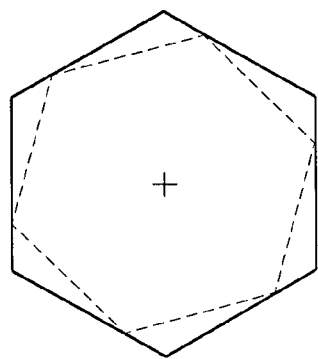
Figure 4C:
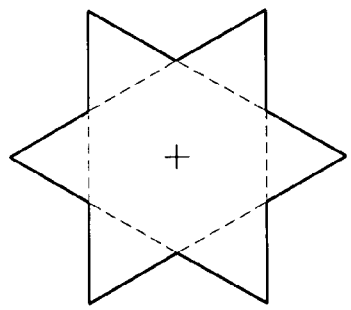
Figure 4D:
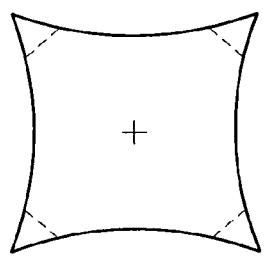
Figure 4E:
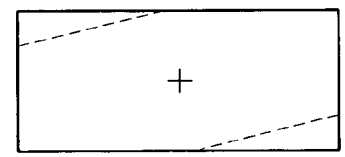
Figure 4F:
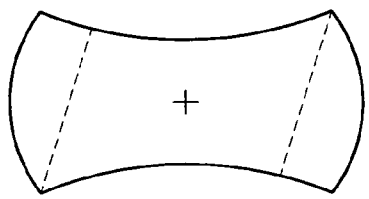
Figure 4G:
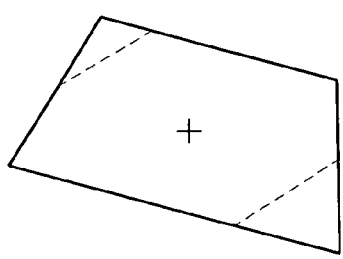
Figure 4H:
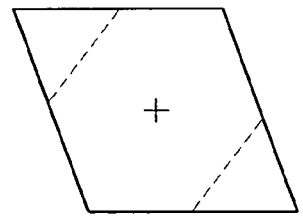

FIGS. 4A-H are schematic views of various alternative embodiments of fluteless endodontic instruments having features and advantages of the present invention. FIG. 4A is a simplified schematic cross-section representation of a fluteless endodontic file having a symmetrical triangular cross-section with notches (hidden lines) and resulting cutting surfaces formed along the three exposed corners thereof FIG. 4B is a simplified schematic cross-section representation of a fluteless endodontic file having a symmetrical hexagonal cross-section with notches (hidden lines) and resulting cutting surfaces formed along the six exposed corners thereof FIG. 4C is a simplified schematic cross-section representation of a fluteless endodontic file having a symmetrical "star-shaped" cross-section with notches (hidden lines) and resulting cutting surfaces formed along the six exposed corners thereof FIG. 4D is a simplified schematic cross-section representation of a fluteless endodontic file having a symmetrical square cross-section with concave flats and acute corners and with notches (hidden lines) and resulting cutting surfaces formed along the four exposed corners thereof. FIG. 4E is a simplified schematic cross-section representation of a fluteless endodontic file having a rectangular cross-section with notches (hidden lines) and resulting cutting surfaces formed along two of the exposed corners thereof FIG. 4F is a simplified schematic cross-section representation of a fluteless endodontic file having a frusto-cylindrical cross-section with concave and convex side surfaces defining four corners and notches (hidden lines) and resulting cutting surfaces formed along two of the exposed corners thereof FIG. 4G is a simplified schematic cross-section representation of a fluteless endodontic file having an asymmetrical polygonal cross-section with notches (hidden lines) and resulting cutting surfaces formed along two of the exposed corners thereof FIG. 4H is a simplified schematic cross-section representation of a fluteless endodontic file having a diamond-shaped cross-section with notches (hidden lines) and resulting cutting surfaces formed along the two outer-most exposed corners thereof.

The concepts and teachings of the present invention are particularly applicable to nickel-titanium alloys and endodontic instruments (files, reamers, obturators, drill bits and the like) fabricated therefrom. However, the invention disclosed herein is not limited specifically to endodontic instruments fabricated from NiTi alloys, but may be practiced with a variety of dental instruments using any one of a number of other suitable medical-grade alloys. Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof Thus, it is intended that the scope of the present invention herein disclosed should not be limited by the particular disclosed embodiments described above, but should be determined only by a fair reading of the claims that follow.

What is claimed is:

1. An endodontic instrument for cleaning and extirpating the walls of a root canal, said instrument comprising an elongated, tapered shaft having a plurality of notches formed along its length, said notches defining one or more cutting surfaces having cutting edges adapted to contact the walls of said root canal when said instrument is rotated and/or reciprocated therein and wherein said shaft has multiple different cross sectional configurations along its length.

2. The endodontic instrument of claim 1 wherein said notches have varying geometric configurations from a proximal end to a distal end of said shaft.

3. An endodontic instrument for cleaning and extirpating the walls of a root canal, said instrument comprising an elongated shaft having a plurality of notches formed along its length, said notches defining one or more cutting surfaces having cutting edges adapted to contact the walls of said root canal when said instrument is rotated and/or reciprocated therein and wherein said notches have varying geometric configurations.

4. The endodontic instrument of claim 3 wherein said elongated shaft is tapered along its length.

5. The endodontic instrument of claim 1 wherein said elongated shaft has a varying taper rate along its length.

6. The endodontic instrument of claim 3 wherein said shaft comprises a medical grade stainless steel.

7. The endodontic instrument of claim 3 wherein said shaft comprises a medical grade titanium-nickel alloy.

8. The endodontic instrument of claim 3 wherein at least a portion of said cutting surfaces are formed such that the shaft, when rotated and/or reciprocated within a root canal, effectively cuts/debrides hard tissue from the walls of the canal.

9. The endodontic instrument of claim 3 wherein at least a portion of said cutting surfaces are formed at an angle with respect to the centerline of said shaft of from about 90° to about 170°.

10. The endodontic instrument of claim 3 wherein at least a portion of said cutting surfaces are formed at an angle of about 120° with respect to the centerline of said shaft.

11. The endodontic instrument of claim 3 wherein at least a portion of said cutting surfaces are formed at alternating angles with respect to the centerline of said shaft.

12. The endodontic instrument of claim 3 wherein one or more of said notches further define relief surfaces formed at an angle with respect to the longitudinal axis of from about 5° to about 45°.

13. The endodontic instrument of claim 3 wherein said shaft has a cross sectional configuration along at least a portion of its length comprising one or more of the following configurations: square, triangular, hexagonal, octagonal, rectangular, trapezoidal, frusto-cylindrical, round, star-shaped or diamond-shaped.

14. The endodontic instrument of claim 3 wherein at least a portion of said notches are disposed relative to adjacent notches such that as the instrument is rotated in the canal, each successive notch presents a cutting surface that is successively higher up the working portion from a distal end to a proximal end thereof.

15. The endodontic instrument of claim 3 wherein said elongated shaft has multiple different cross sectional configurations along at least a portion of its length from said proximal to said distal end.

16. The endodontic instrument of claim 3 wherein said elongated shaft has a non-uniform taper along at least a portion of its length.

17. The endodontic instrument of claim 3 wherein at least a portion of said notches vary in depth from a proximal end to a distal end of said shaft.

18. The endodontic instrument of claim 3 wherein at least a portion of said cutting surfaces are formed at an angle with respect to the centerline of said shaft from about 110° to about 160°.

19. The endodontic instrument of claim 3 wherein said cutting surfaces are formed at alternating angles of about 120° and −120° with respect to the centerline of said shaft.

* * * * *